United States Patent [19]

Gillings et al.

[11] 4,198,397

[45] Apr. 15, 1980

[54] ARTHROPODICIDAL GRANULAR FORMULATION

[75] Inventors: Christopher Gillings, Linton; John H. Palmer, Saffron Walden, both of England

[73] Assignee: Fisons Limited, London, England

[21] Appl. No.: 877,812

[22] Filed: Feb. 14, 1978

[30] Foreign Application Priority Data

Feb. 16, 1977 [GB] United Kingdom ............... 6366/77
Mar. 17, 1977 [GB] United Kingdom ............. 11392/77
Sep. 27, 1977 [GB] United Kingdom ............. 40111/77

[51] Int. Cl.$^2$ ............................................. A01N 9/28
[52] U.S. Cl. ...................................... 424/83; 424/282

[58] Field of Search ................................. 424/282, 83; 260/340.5 R

[56] References Cited

U.S. PATENT DOCUMENTS 3,948,952  4/1976  Gates et al. ........................ 424/282

Primary Examiner—V. D. Turner
Attorney, Agent, or Firm—Wenderoth, Lind & Ponack

[57] ABSTRACT

Pesticidal bendiocarb granules comprise either (a) base granules to which the bendiocarb adheres by means of a sticker comprising a hydrocarbon of viscosity at least 20 centipoises, the bendiocarb granules bearing a surface coating of a flowability agent, or (b) absorbent base granules impregnated with the bendiocarb.

12 Claims, No Drawings

ARTHROPODICIDAL GRANULAR FORMULATION

This invention relates to bendiocarb granules, their preparation and their use.

Bendiocarb, 2,2-dimethyl-1,3-benzodioxol-4-yl N-methylcarbamate, is a known pesticide for example insecticide. It would be useful to be able to employ the pesticide in the form of granules, but such granules are not commercially available. We have now discovered such granules which are surprisingly advantageous, e.g. by way of chemical stbility of the bendiocarb.

Accordingly, the invention provides pesticidal bendiocarb granules comprising either (a) base granules to which the bendiocarb adheres by means of a sticker comprising a hydrocarbon of viscosity at least 20 centipoises, the bendiocarb granules bearing a surface coating of a flowability agent, or (b) absorbent base granules impregnated with the bendiocarb.

In one aspect, the invention provides pesticidal bendiocarb granules comprising absorbent base granules impregnated with the bendiocarb.

The invention provides also a process for preparing the impregnated granules, which process comprises dissolving bendiocarb in a solvent and mixing the resultant solution with absorbent base granules such that the solution is absorbed by the base granules to distribute the bendiocarb within the lattice structure of the base granules.

In another aspect, the invention provides pesticidal bendiocarb granules in which the bendiocarb adheres to base granules by means of a sticker comprising a hydrocarbon of viscosity at least 20 centipoises and which bear a surface coating of a flowability agent. Viscosities in this specification are as measured at 20° C. on a Brookfield viscometer, RVT model, number 1 spindle, unless otherwise stated. Usually the base granules have thereon a layer comprising the sticker, on the sticker layer is a layer comprising the bendiocarb, and on the bendiocarb layer is a layer comprising the flowability agent.

The invention provides also a process for preparing these coated granules, which process comprises coating the base granules successively with a layer comprising the sticker, then with a layer comprising bendiocarb and finally with a surface layer comprising a flowability agent.

The invention provides also a method of combating pests at a locus infested or liable to be infested with them, which method comprises applying an effective amount of the present granules to the locus.

The sticker in the present coated granules results in surprisingly good adherence of the constituents. In addition, it enables there to be obtained pesticidal bendiocarb granules which flow freely, with no tendency to agglomerate in storage or when used in conventional pesticidal granule applicators. Moreover, the present coated granules are surprisingly stable to chemical decomposition of the bendiocarb, e.g. no more than 15% of the bendiocarb decomposing after a year on storage of the granules in an accelerated storage test at 40° C.

The amount of bendiocarb in the coated granules is normally 0.5 to 10% of the granules, preferably 3 to 5%, e.g 3%. It may be present with other physiologically active materials, particularly other pesticides e.g other insecticides or acaricides. Percentages in this specification are by weight unless otherwise indicated.

Convenient granule bases in the coated granules are solid, non-absorbent, non-porous materials, e.g limestone, sand, calcite, marble or slate. The bulk density of the granule base is generally at least 1 g/ml. Limestone grit or sand is preferred, especially limestone grit. The base is normally of size 250–1,000 microns. Sieve sizes as referred to in this specification are according to British Standard 410. The coated bendiocarb granules may contain for example 80–97% of base granules.

The sticker generally comprises a hydrocarbon of viscosity 20–4,000, preferably 20–500, centipoises. The hydrocarbon may be naturally occurring or may have been obtained synthetically, e.g by polymerising one or more unsaturated monomers. Normal hydrocarbons may be used, though branched hydrocarbons are preferred. Aliphatic hydrocarbons are preferred. Mixtures of hydrocarbons may be employed. Usually the sticker consists of the hydrocarbon, though other sticker materials may also be present e.g in a content up to 25% by weight of the sticker.

The hydrocarbon may be for example, a mineral oil or 300 second fuel oil. Preferably, however, the hydrocarbon is a polymer of butene, which may be 1-butene, 2-butene or isobutene. Copolymers of 2 or of all 3 of these may be employed. Other comonomers may also be employed, though this is not preferred. Mixtures of the polymers may be used. Preferably the polymer of butene consists of polymerised butene, especially derived from a mixture of 1 and 2-butenes or from isobutene, and particularly preferred is the polymer consisting of polyisobutene. Commercial polyisobutenes, while consisting essentially of polymerised isobutene, often contain minor amounts, e.g up to 10% by weight, of polymerised normal butene. For the present purpose, they are regarded as polyisobutene. The polymerised butene is conveniently a low viscosity liquid rather than a solid at ambient temperature. The polymerised butene is preferably of viscosity 20–500 cps, e.g Hyvis 05 (from BP Chemicals) which has a viscosity of 200 cps, Hyvis 04 (from BP Chemicals) which has a viscosity of 50 cps, or Indopol L10 (from Amoco) which has a viscosity of 50 cps.

The choice of viscosity depends on the stickiness required and the ease and method of application of the hydrocarbon to the base granules. So that a layer of the hydrocarbon can be applied conveniently to base granules without using a diluent to reduce its viscosity, its viscosity is generally 20 to 500, preferably 40 to 150, centipoises, as measured at 20° C. Hydrocarbons of higher viscosity can be applied as solutions in an aliphatic or aromatic hydrocarbon solvent, e.g kerosene, so that the viscosity of the solution is within this general range, but this is generally less convenient since for example slow evaporation of the solvent from the resultant granules can occur in storage. The viscosity of the hydrocarbon is preferably 20–500 cps at the temperature at which the hydrocarbon is applied to the base granules. The hydrocarbon can be applied to the base granules as an oil in water emulsion, with subsequent removal of the water by evaporation, though this technique is not preferred. The coated granules may contain for example 0.2–5% of sticker.

The bendiocarb in the coated granules is normally applied in powder form. It may be applied in admixture with a mineral filler such as China clay, precipitated silica or calcined Diatomite, but this is not preferred. The bendiocarb is preferably hammer milled bendiocarb e.g of particle size less than 50 microns.

The coated granules have a surface coating of a highly absorptive powder filler used in sufficient amount to ensure that the granules flow freely through the equipment used to apply them and do not agglomerate in storage. The quantity of such a flowability agent required depends on the degree of stickiness of the granules before application of the agent and can sometimes vary between batches. Suitable flowability agents are calcined Diatomite; calcium or magnesium silicate of synthetic or natural origin; precipitated silica; and China clay. The calcium or magnesium silicate should not of course be so alkaline as adversely to effect the chemical stability of the bendiocarb. Silica is the preferred flowability agent, e.g precipitated silica such as that sold as Neosyl by J. Crosfield. The coated granules may contain for example 0.1-5% of flowability agent.

The coated granules are preferably prepared by charging in turn to a flighted drum mixer, allowing time between additions, (i) the base granules, (ii) the sticker, (iii) the bendiocarb and (iv) the flowability agent, and finally sieving, e.g through a 1,400 micron sieve, to remove any oversize materials. The production is usually carried out at ambient temperature, though for instance the sticker and base granules may be preheated, e.g to 35°-40° C., prior to mixing to achieve a more even coating.

In a preferred embodiment, the coated granules contain 0.5 to 10% bendiocarb and are limestone base granules having thereof a layer of polymerised butene of viscosity 20-300 cps, on that layer a layer of bendiocarb and on that layer a surface coating of precipitated silica.

Before the present invention, pesticidal bendiocarb granules in which the bendiocarb is contained within absorbent base granules were entirely unknown. The impregnated bendiocarb granules are surprisingly advantageous. Coated granules tend to require variation, e.g. in amount of surface coating, between batches in their manufacture; the present impregnated granules can be manufactured more reproducibly and hence more easily. Furthermore, coated granules contain a sticker which may give rise to aggregation of the granules; the present impregnated granules have less tendency to aggregate than coated granules. Moreover, the impregnated granules exhibit remarkably good chemical stability of the bendiocarb, (e.g as shown in the Examples, impregnated granules of the invention undergo no more than 10%, preferably no more than 8%, bendiocarb decomposition on storage for 6 months, preferably 12 months, at 40° C. in an accelerated storage test). Impregnated granules can be obtained which flow freely and have no tendency to agglomerate in storage or when used in conventional pesticidal granule applicators.

The impregnated granules usually contain 0.1-30%, 2-30%, preferably 5-20%, e.g 10%, bendiocarb. Other physiologically active materials, particularly other pesticides e.g other insecticides or acaricides, may be present with the bendiocarb.

The base granules in the impregnated granules must be capable of absorbing the bendiocarb in the process according to the invention, and must not of course result in excessive decomposition of the bendiocarb. Suitable base granules are generally lighter than those suitable for coated bendiocarb granules. The base granules in the impregnated granules usually have a bulk density less than 1 g/ml, though preferably not less than 0.4 g/ml.

The base granules in the impregnated granules should be of appropriate free-flow sorptive capacity for the solvent employed in the process according to the invention. Free-flow sorptive capacity is the maximum volume of the solvent that the absorbent base can contain with no loss in free-flowing ability. It is expressed as volume of solvent per 100 weight units of absorbent base. In general, the base granules should have a free-flow sorptive capacity for the solvent of at least 20 ml per 100 g. The present base granules generally have a sorptive capacity for dichloromethane at 20° C. of at least 20 ml per 100 g. The impregnated granules may contain for example 70-99.9 for instance 70-98% of base granules.

Suitable base granules for the impregnated granules include absorbent botanical base granules such as corn cob grit, though their low free-flow sorptive capacities (e.g that of corn cob grit is about 20 ml per 100 g at 20° C. for dichloromethane) generally means that a multistage impregnation process is required. Remarkably better than absorbent, mineral, silicate bases such as attapulgite or Fullers Earth, as regards the resultant bendiocarb granules being outstandingly stable to bendiocarb decomposition, are base granules of calcined diatomaceous silica especially that marketed by Eagle-Picher as Celaton MP78, and base granules of Agsorb 24/48 S-100 (from Oil-Dri Corporation, Chicago, USA), Experimental Attapulgus X-1919 (from Engelhard), gypsum or deactivated mineral silicates, and accordingly such base granules are preferred.

The bulk density of calcined diatomaceous silica (e.g. Celatom MP78) 0.4 g/ml, of Agsorb 24/48 S-100, 0.95 g/ml, of Experimental Attapulgus X-1919, 0.88 g/ml, and of gypsum, 0.82 g/ml; in contrast, limestone grit, a suitable base granule material for bendiocarb coated granules, has a bulk density of about 1.4 g/ml. The free-flow sorptive capacity for dichloromethane at 20° C. of Celatom MP78 is 90 ml per 100 g, of Agsorb 24/48 S-100, 25 ml per 100 g, of Experimental Attapulgus X-199, 28 ml per 100 g, and of gypsum, 25 ml per 100 g.

The impregnated granules are preferably prepared by dissolving bendiocarb in a volatile solvent, mixing the resultant solution with absorbent base granules such that the solution is absorbed by the base granules, and evaporating off the solvent to leave the bendiocarb within the lattice structure of the base granules. In this embodiment, the solvent employed should be sufficiently volatile so that it can be evaporated off conveniently from the granules which have absorbed the solution of the bendiocarb in the solvent, e.g. by being placed in a forced air draught and periodically agitated or in a fluidised bed-type drier and warm air passed through. A preferred solvent is dichloromethane, acetone or chloroform, especially dichloromethane.

The impregnated granules are preferably prepared by dissolving bendiocarb in a volatile solvent (e.g. dichloromethane to give a solution containing 200-220 g, for instance 200 g, of bendiocarb per liter), adding the resultant solution to absorbent base granules revolving in a drum, when the base granules have absorbed the solution, evaporating off the solvent (preferably in a forced air draught) and finally screening to remove any oversize material.

The production of the impregnated granules is usually carried out at ambient temperature. In general, the solubility of bendiocarb in the solvent is at least 150 g per liter as measured at 15° C.

The present granules (i.e. the impregnated granules or the granules containing the present particular sticker) are preferably substantially all of less than 1,400 microns in major dimension. Sieve sizes as referred to in this specification are according to British Standard 410. Most preferably, no more than 4% is smaller than 250 microns in major dimension and no more than 1% is smaller than 150 microns in major dimension.

The present granules may be employed against a wide range of pests. The pest animals are usually arthropods, especially insects or acarids, particularly insects. The pests may be public health pests; thus, the granules can be applied in or around buildings. Preferably, however, the granules are employed against agricultural pests, particularly agricultural insect pests; thus, the granules can be applied on land or the soil or to plants. In a preferred embodiment, the granules are applied to a locus at which crops (i.e. desired plants) are growing or are to grow, to protect them from attack by pests, particularly seedling pests, soil pests, stem boring pests or plant hoppers. The crops may be for instance vegetables, notably potatoes, brassicas, onions or beans, cereals, notably wheat, barley, oats, maize or rice, or sugar beet. Pests against which the granules are active include Coleoptera, Diptera, Lepidoptera or Hemiptera (Homoptera), for example wireworms (e.g. Agriotes spp), corn rootworm (Diabrotica spp), pygmy beetle (Atomaria), flea beetles (e.g. Chaetocnema spp), plant hoppers (e.g. *Nilaparvata lugens* or *Nephotettix virescens*), cabbage root fly (*Erioischia brassicae*), frit fly (*Oscinella frit*), and stem borers (e.g *Ostrinia nubilalis* or Busseola spp), springtails (e.g Onychiurus spp), millipedes (e.g. *Blaniulus guttulatus*), symphylids (e.g. *Scutigerella immaculata*) and cockroaches. Especially, the granules can be used on maize against wireworms (e.g Agriotes spp), frit fly (*Oscinella frit*), corn rootworm (Diabrotica spp) or stem borers (e.g *Ostrinia nubilalis* or Busseola spp) or on sugar beet against pygmy beetle (*Atomaria linearis*), wireworms (e.g Agriotes spp), millipedes (e.g *Blaniulus guttulatus*), springtails (e.g Onychiurus spp) or symphylids (e.g *Scutigerella immaculata*). For the control of soil and seedling pests in for example maize or sugar beet, the granules can be applied in the furrow at planting or as a surface band. For the control of stem borers in for example maize, the granules can be applied into the funnels of the growing crop by broadcast application over the crop particularly at the times of moth flight warnings. For use in rice, the granules can be applied to the paddy water or to the ground before flooding.

The granules may be applied in and around buildings at a rate for example of 10–1,000 mg of bendiocarb per square meter. They may be applied at a locus where plants are growing or are to grow at a rate for example of 0.1–4, e.g 0.2–1.0, kg of bendiocarb per hectare.

The granules may be applied through conventional granule applicators.

The invention is illustrated by the following Examples, in which the bendiocarb contents are as assessed on analysis of the granules produced.

EXAMPLE 1

Impregnated bendiocarb granules were prepared comprising:
Bendiocarb technical to give a bendiocarb content of: 9.7%
Celatom MP 78: 90.3%

The Celatom MP 78 was charged to a double-cone shaped mixer. The bendiocarb was dissolved in dichloromethane to give a 200 g per liter solution. This solution was added slowly over 5–10 minutes to the Celaton MP 78 base granules whilst mixing. Up to 30 minutes mixing was allowed for uniform distribution and absorption of the solution. The resultant granules were still free flowing. They were placed in a forced air draught and occasionally agitated, to evaporate off the dichloromethane. Finally, the granules were sieved through a 1,400 micron sieve.

EXAMPLE 2

The procedure of Example 1 was followed except that the base granules were corn cob grit of size 500 to 1,000 microns (from Mount Pulaski Mills, Ill., USA) and the solution was added in 3 stages with solvent evaporation after each stage (to make a triple impregnation process in all) in order to produce granules comprising 9.0% bendiocarb and 91.0% corn cob grit.

EXAMPLES 3 AND 4

The chemical stability of the bendiocarb in the granules prepared in the preceding Examples was tested in accelerated storage tests by analysing to find the percentage decomposition of the bendiocarb in the granules after storage at 40° C.

The results are shown in the Table below:

| Example | Granules of Example | 40° C. STORAGE STABILITY Percent by weight Decomposition after | | | | |
|---|---|---|---|---|---|---|
| | | 1 month | 2 months | 3 months | 6 months | 12 months |
| 3 | 1 | 3 | 2 | 1 | 6 | 8 |
| 4 | 2 | 0 | — | 0 | 0 | 0 |

EXAMPLE 5

Following the procedure of Example 1, impregnated bendiocarb granules were prepared, comprising:
Bendiocarb technical to give a bendiocarb content of: 2.85%
Agsorb 24/48 S-100: 97.15%

EXAMPLE 6

Following the procedure of Example 1 except that the bendiocarb solution was added in 2 stages with solvent evaporation after each stage (to make a double impregnation process in all), impregnated bendiocarb granules were prepared comprising:
Bendiocarb technical to give a bendiocarb content of: 7.6%
Agsorb 24/48 S-100: 92.4%

EXAMPLE 7

Following the procedure of Example 6, impregnated bendiocarb granules were prepared comprising:
Bendiocarb technical to give a bendiocarb content of: 9.2%
Gypsum granules, size −22+44 British Standard (from British Gypsum Limited): 90.8%

EXAMPLE 8

The chemical stability of the bendiocarb in the impregnated granules of Example 7 was tested in accelerated storage tests by analysing to find the percentage decomposition of the bendiocarb in the granules after storage at elevated temperatures.

The results are shown in the Table below.

| Storage for | Percent by weight Decomposition |
|---|---|
| 1 month at 40° C. | 5 |
| 3 months at 40° C. | 2 |
| 2 weeks at 54° C. | 5 |

EXAMPLE 9

Following the procedure of Example 6, impregnated bendiocarb granules were prepared comprising:
Bendiocarb technical to give a bendiocarb content of: 9.5%
Experimental Attapulgus X-1919 (from Engelhard): 90.5%

EXAMPLE 10

Following the procedure of Example 8, the granules of Example 9 gave the following results:

| Percent by weight Decomposition after | | |
|---|---|---|
| 2 weeks at 54° C. | 1 month at 40° C. | 3 months at 40° C. |
| 2 | 2 | 7 |

EXAMPLE 11

Following the procedure of Example 8, the granules of Example 6 gave the following results:

| Percent by weight Decomposition | | | |
|---|---|---|---|
| 2 weeks at 54° C. | 1 month at 40° C. | 3 months at 40° C. | 6 months at 40° C. |
| 8 | 0 | 3 | 5 |

EXAMPLE 12

Bendiocarb granules on a 1 kg scale were prepared comprising:
Bendiocarb technical to give a bendiocarb content of: 4.8%
Sand: 93.8%
Polybutene 24 (from Chevron Chemicals)/kerosene blend, 3:2 by weight: 1.0%
Calflo E (synthetic calcium silicate from Johns Manville): 0.4%

The sand was charged to a revolving double-cone shaped mixer. The Polybutene 24/kerosene blend sticker was added to the sand granule base and allowed 15–30 minutes to mix. Hammer-milled bendiocarb was then added over 5–10 minutes in a similar way and allowed 15–30 minutes to mix. The Calflo E flowability agent was added in a similar way in 3 or 4 equal batches, allowing 15 minutes mixing between each batch. The granules were finally allowed 30 minutes mixing and then discharged through a coarse sieve (1,400 micron) to remove any chance agglomerates.

On a larger scale, the times quoted above can advantageously be reduced.

EXAMPLE 13

Following the procedure of Example 12, bendiocarb granules were prepared comprising:
Bendiocarb technical to give a bendiocarb content of: 4.9%
Limestone grit, 250–1,000 microns: 92.4%
Polybutene 24/kerosene blend, 3:2 by weight: 2.5%
Calflo E: 0.2%

EXAMPLE 14

Bendiocarb granules on a 50 kg scale were prepared comprising:
Bendiocarb technical to give a bendiocarb content of: 4.7%
Limestone grit: 90.8%
Polybutene 24/kerosene blend, 3:2 by weight: 2.5%
Neosyl (precipitated silica, from J. Crosfield): 2.0%

The procedure was that of Example 12 but using a conventional builders concrete mixer.

EXAMPLES 15–17

Following the procedure of Example 14, bendiocarb granules were prepared comprising:

|  | Example 15 | 16 | 17 |
|---|---|---|---|
| Bendiocarb technical to give a bendiocarb content of | 5.0% | 4.8% | 2.9% |
| Limestone grit | 90.5% | 90.7%+ | 92.6%+ |
| Hyvis 05 (from BP Chemicals) | 2.5% | 2.5%+ | 2.5%+ |
| Neosyl | 2.0% | 2.0% | 2.0% |

+ indicates that the Hyvis 05 and limestone grit were preheated to 35–40 C

EXAMPLE 18

Following the procedure of Example 14, bendiocarb granules were prepared comprising:
Bendiocarb technical to give a bendiocarb content of: 2.6%
Limestone grit: 94.4%
Polybutene 24/kerosene blend, 3:2 by weight: 1.5%
Neosyl: 1.5%

EXAMPLES 19 AND 20

Following the procedure of Example 14, bendiocarb granules were prepared comprising:

|  | Example | |
|---|---|---|
|  | 19 | 20 |
| Bendiocarb technical to give a bendiocarb content of | 4.9% | 3.1% |
| Limestone grit | 90.6% | 92.9% |
| Hyvis 04 (from BP Chemicals) | 2.5% | 2.0% |
| Neosyl | 2.0% | 2.0% |

EXAMPLE 21

In comparison, granules analogous to those of Example 15 but containing a different sticker, Carbowax 400 (polyethylene glycol), were prepared comprising:
Bendiocarb technical to give a bendiocarb content of: 4.7%
Limestone grit: 91.8%
Carbowax 400 (from Union Carbide): 2.5%
Neosyl: 1.0%

EXAMPLES 22-31

The chemical stability of the bendiocarb in the granules of Examples 12-21 was tested in accelerated storage tests by analysing to find the percentage decomposition of the granules after storage at 40° C.

The results are shown in the Table below:

| Example | Granules of Example | 40° C. STORAGE STABILITY Percent by weight Decomposition after | | |
|---|---|---|---|---|
| | | 1 month | 3 months | 12 months |
| 22 | 12 | 2 | 6 | 2 |
| 23 | 13 | 2 | 8 | 12 |
| 24 | 14 | 0 | 0 | 13 |
| 25 | 15 | 0 | — | 10 |
| 26 | 16 | 0 | 0 | 0 |
| 27 | 17 | 0 | 0 | 0 |
| 28 | 18 | — | — | 12 |
| 29 | 19 | 0 | 0 | 0 |
| 30 | 20 | 3 | 3 | 5 |
| 31 | 21 | 6 | 13 | 30 |

It can be seen that the coated granules of the invention, those of Examples 12-20, are much more stable than the comparative coated granules, those of Example 21.

EXAMPLE 32

The granules of Example 17 were applied with a Horstine-Farmery granule applicator, wheelbarrow model, into the furrow at the time of drilling maize, the granules being applied at the bendiocarb rate listed in the table. Each trial was carried out as standard randomised block experiments with four replicates, each plot being 20 m in length and containing four rows of maize. Assessments were made 5 weeks after sowing of the attack by wireworms (Agriotes spp) on the 2 centre rows in comparison with that on the 2 centre rows of untreated control plots; hence the percent control was calculated. The results obtained were as follows:

| Bendiocarb rate, g/ha | % Control of Wireworm |
|---|---|
| 200 | 84.7 |
| 300 | 90.9 |

EXAMPLE 33

The granules of Example 17 were applied using 'pepper pot' applicators in a similar way to that in Example 32 against frit fly (Oscinella frit) in maize, assessments being carried out 3 weeks and 5 weeks after sowing. The results obtained were as follows:

| Bendiocarb rate, g/ha | % Control of Frit Fly | |
|---|---|---|
| | After 3 weeks | After 5 weeks |
| 100 | 25.3 | 45.6 |
| 200 | 62.3 | 76.3 |
| 300 | 59.2 | 76.0 |
| 400 | 74.0 | 80.3 |

EXAMPLE 34

The granules of Example 17 were applied with a Horstine-Farmery granule applicator at the rate of 360 g of bendiocarb per hectare into the furrow at the time of drilling sugar beet. 6 weeks after sowing, the percentage control of wireworm (Agriotes spp) was assessed by counting the number of plants which had emerged per 10 meters of the row. The number in the treated rows was 216% of that in untreated control rows.

EXAMPLE 35

The granules of Example 15 were applied at the bendiocarb rate listed in the table below to maize at the 7-8 leaf stage already infested with stem borer larvae (Busseola spp). The granules were broadcast by hand using a shaker into the plant funnel, at the bendiocarb rate listed in the table. 24 Hours after treatment, the percentage kill of the larvae was assessed by removing the central shoots of the plants and examining the interior for the numbers of larvae present compared to the corresponding number found in untreated controls. The mean percentage of dead larvae is shown in the following table:

| Bendiocarb rate, g/ha | % Dead Larvae |
|---|---|
| 37 | 85 |
| 76 | 90 |
| 114 | 92 |
| 152 | 95 |

We claim:
1. In an arthropodicidal granular material comprising 2,2-dimethyl-1,3-benzodioxol-4-yl N-methyl-carbamate as arthropodicide and comprising base granules coated on their surface with a sticker layer, said sticker layer being in turn coated with a layer of said arthropodicide, said arthropodicide layer in turn being coated with flowability agent which is a highly absorptive powder filler in a sufficient amount to ensure free flowability of the granules, the improvement according to which the sticker comprises a hydrocarbon having a viscosity of 20 to 4,000 centipoises.

2. An arthropodicidal granular material according to claim 1 wherein the hydrocarbon sticker is a branched aliphatic hydrocarbon.

3. An arthropodicidal granular material according to claim 1 wherein the hydrocarbon sticker is a polymer of butene.

4. An arthropodicidal granular material according to claim 1 wherein the polymer consists of polymerized monomers consisting of one or more of 1-butene, 2-butene and isobutene.

5. An arthropodicidal granular material according to claim 1 wherein the flowability agent is selected from the group consisting of calcined diatomite, calcium silicate, magnesium silicate, silica and China Clay.

6. An arthropodicidal granular material according to claim 1 wherein the base granules are solid, non-absorbent, non-porous granules of size 250-1000 microns, and of bulk density at least 1 g per ml.

7. An arthropodicidal granular material according to claim 1 wherein the base granules are of sand, calcite, marble, or limestone grit.

8. An arthropodicidal granular material according to claim 1 comprising by weight 0.5-10% 2,2-dimethyl-1,3-benzodioxol-4-yl N-methyl-carbamate, 80-97% base granule, 0.2-5% sticker and 0.1-5% flowability agent.

9. An arthropodicidal granular material according to claim 1 wherein substantially all of the granules are less than 1400 microns in major dimension, not more than 4% by weight are smaller than 250 microns in major dimension, and no more than 1% by weight are smaller than 150 microns in major dimension, the granules comprise limestone grit base granules on each of which is a layer comprising polyisobutene of viscosity 20-500 centipoises as sticker, on the sticker layer is a layer comprising the said arthropodicide, and on the arthropodicide layer is a layer comprising precipitated silica as flowablity agent, the granules comprising by weight 0.5-10% of the pesticide, 80-97% of the limestone grit, 0.2-5% of the polyisobutene of viscosity 20-500 centipoises and 0.1-5% of the precipitated silica.

10. An arthropodicidal granular material according to claim 1, substantially all of the granules of which are less than 1400 microns in major dimension, no more than 4% by weight of which are smaller than 250 microns in major dimension, and no more than 1% by weight of which is smaller than 150 microns in major dimension.

11. A process for preparing an arthropodicidal granular material as claimed in claim 1, which process comprises coating the base granules successively with a layer comprising the sticker, then with a layer comprising the arthropodicide and finally with a surface layer comprising the flowability agent.

12. A method of combatting arthopoda at a locus infested or liable to be infested with them, which method comprises applying to the locus an arthropodicidally effective amount of the granular material as defined in claim 1.

* * * * *